(12) United States Patent
Park et al.

(10) Patent No.: US 11,628,035 B2
(45) Date of Patent: Apr. 18, 2023

(54) ENDOSCOPE SURGERY DEVICE

(71) Applicant: INDUSTRY-ACADEMIC COOPERATION FOUNDATION, YONSEI UNIVERSITY, Seoul (KR)

(72) Inventors: No Cheol Park, Seoul (KR); Kyo Chul Koo, Seoul (KR); Dongwook Kim, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 849 days.

(21) Appl. No.: 16/574,082

(22) Filed: Sep. 18, 2019

(65) Prior Publication Data
US 2020/0093561 A1 Mar. 26, 2020

(51) Int. Cl.
| | | |
|---|---|---|
| *A61B 90/00* | (2016.01) | |
| *A61N 7/00* | (2006.01) | |
| *A61B 1/307* | (2006.01) | |
| *A61B 17/00* | (2006.01) | |
| *A61M 25/06* | (2006.01) | |
| *A61B 18/00* | (2006.01) | |

(52) U.S. Cl.
CPC .............. *A61B 90/08* (2016.02); *A61B 1/307* (2013.01); *A61N 7/00* (2013.01); *A61B 2017/00292* (2013.01); *A61B 2018/00505* (2013.01); *A61B 2090/08021* (2016.02); *A61M 25/0662* (2013.01); *A61N 2007/0043* (2013.01)

(58) Field of Classification Search
CPC ...... A61M 2025/0687; A61M 25/0102; A61B 90/08; A61B 2090/0901; A61B 2090/08021; A61B 1/307; A61B 2018/00505; A61N 7/00
See application file for complete search history.

(56) References Cited

U.S. PATENT DOCUMENTS

| | | | | |
|---|---|---|---|---|
| 4,535,759 A | * | 8/1985 | Polk ...................... | A61M 29/00 606/119 |
| 5,243,997 A | * | 9/1993 | Uflacker .......... | A61B 17/22012 600/585 |
| 2011/0015786 A1 | * | 1/2011 | Kawai .................... | A61B 34/70 700/256 |
| 2011/0264038 A1 | * | 10/2011 | Fujimoto ........ | A61M 25/09041 604/95.01 |
| 2013/0030329 A1 | * | 1/2013 | Zumeris ............. | A61B 1/00131 601/2 |

(Continued)

FOREIGN PATENT DOCUMENTS

| | | | | |
|---|---|---|---|---|
| EP | 2428157 A1 | * | 3/2012 | ......... A61B 1/00089 |
| JP | 09098979 A | | 4/1997 | |

(Continued)

*Primary Examiner* — Catharine L Anderson
*Assistant Examiner* — Arjuna P Chatrathi
(74) *Attorney, Agent, or Firm* — Leepi

(57) ABSTRACT

An endoscope surgery device includes a vibration unit and a surgery unit. The vibration unit generates a vibration. The surgery unit includes a sheath and a surgery member. The sheath has a tube shape with a hollow extended in a longitudinal direction, and is entirely vibrated due to the vibration from the vibration unit with inserted into the ureter. The surgery unit passes through the hollow of the sheath, and is extended to an end of the sheath for an surgical procedures on the ureter.

7 Claims, 4 Drawing Sheets

(56) References Cited

U.S. PATENT DOCUMENTS

2014/0094779 A1* 4/2014 Sakamoto ............. A61M 25/01
604/528
2015/0133950 A1* 5/2015 Shelton ............ A61B 17/22012
606/128

FOREIGN PATENT DOCUMENTS

| | | | |
|---|---|---|---|
| JP | 2002282204 | A | 10/2002 |
| JP | 2003510159 | A | 3/2003 |
| JP | 4095729 | B | 6/2008 |
| JP | 4504361 | B | 7/2010 |
| KR | 10-2010-0018153 | A | 2/2010 |
| KR | 10-1664348 | B | 10/2016 |
| KR | 10-2017-0074715 | A | 6/2017 |

* cited by examiner

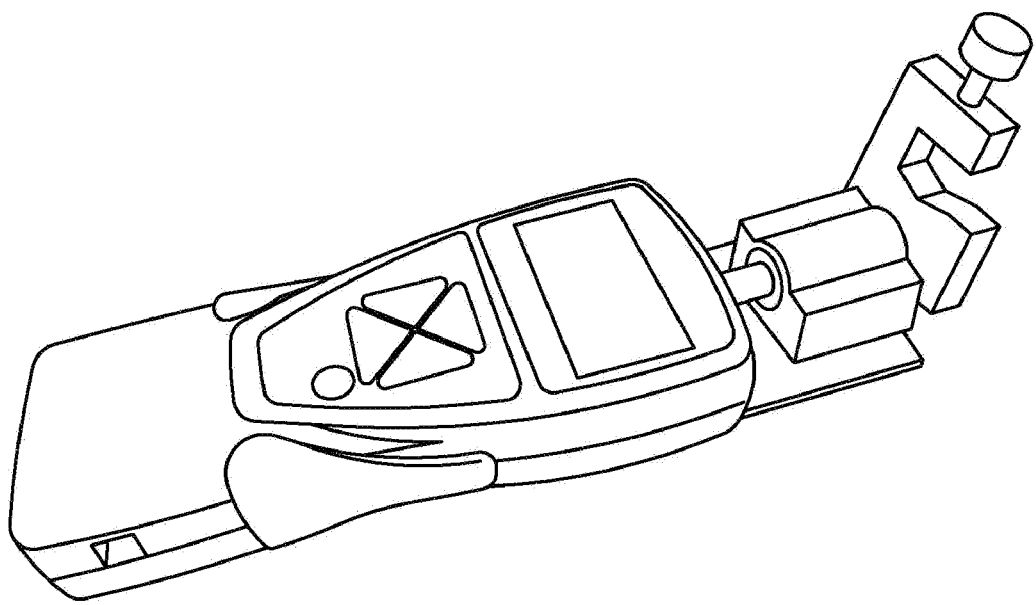
FIG. 4

ENDOSCOPE SURGERY DEVICE

This application claims priority under 35 U.S.C. § 119 to Korean Patent Application No. 10-2018-0112697, filed on Sep. 20, 2018, the disclosure of which is incorporated by reference herein in its entirety.

BACKGROUND

1. Field of Disclosure

The present disclosure of invention relates to an endoscope surgery device, and more specifically the present disclosure of invention relates to an endoscope surgery device entering the ureter and reducing the risk of ureteral injury.

2. Description of Related Technology

An endoscope surgery is widely used since incision portion is to be minimized and recovery is relatively fast.

Recently, a surgery device used for endoscope surgery on organs like kidney, heart and so on, has been developed. Here, the surgery device is inserted into the urinary tract system, specifically the ureter.

However, in the inserting of the surgery device, ureteral injury is inevitable and is reported to occur in 46% of all surgical cases.

For example, in retrograde intrarenal surgery (RIRS), a diameter of an external sheath is larger than that of the ureter, and thus the ureter may be damaged in the inserting of the ureteral access sheath. Further, the damaged portions of the ureter may lead to long-term complications such as ureteral stricture.

Related prior arts on the above mentioned technology are Japanese patent No. 4,095,729, Japanese patent No. 4,504,361 and Japanese laid-open patent No. 2003-510159.

SUMMARY

The present invention is developed to solve the above-mentioned problems of the related arts. The present invention provides an endoscope surgery device capable of entering the ureter and capable of reducing ureteral injury.

According to an example embodiment, endoscope surgery device includes a vibration unit and a surgery unit. The vibration unit generates a vibration. The surgery unit includes a sheath and a surgery member. The sheath has a tube shape with a hollow extended in a longitudinal direction, and is entirely vibrated due to the vibration from the vibration unit when inserted into the ureter. The surgery unit passes through the hollow of the sheath, and is extended to an end of the sheath for surgical procedures within the ureter.

In an example, the vibration unit may generate an ultrasonic vibration.

In an example, the ultrasonic vibration may have a vibration intensity between about 250 mV and about 500 mV, and may have the frequency of vibrations between about 300 Hz and about 18,000 Hz.

In an example, the vibration unit may vibrate the sheath along the longitudinal direction.

In an example, the vibration unit may include a vibration member generating the vibration, a pressure sensor disposed between the vibration member and the surgery unit, to measure an inserting pressure of the surgery unit, and a control member configured to stop the vibration of the vibration member, when the measured pressure from the pressure sensor is over a threshold.

In an example, the vibration unit may include a vibration transmitting member disposed between the pressure sensor and the surgery unit, and fixed to an end of the surgery unit.

In an example, an axis of the pressure sensor may not be coincided with that of the surgery unit.

In an example, the vibration member and the pressure sensor may have the same axis coincided with the axis of the sheath.

In an example, the vibration unit may further include a contact sensor sensing a contacting state of a hand of an operator. The control member may be configured to stop the vibration of the vibration unit when the hand of the operator is slipped from a surface of the vibration unit.

According to the present example embodiments, a vibration is applied to a sheath of an endoscope surgery device, and thus a friction force between the ureter and the sheath may be decreased. Thus, the sheath may be inserted into the ureter more easily and the damage to the ureter may be prevented or minimized.

In addition, a pressure sensor is configured to stop vibration when the applied vibration on the sheath is increased over a threshold, and the combination between a vibration unit and a surgery unit is automatically released. Thus, further excessive placement of the sheath may be prevented and the damage of the ureter may be prevented.

In addition, a fixing member and a vibration transmitting member are detachably combined with each other, and thus the fixing member and the vibration transmitting member may be easily replaced.

In addition, the vibration unit and the surgery unit share the same axis, and thus the vibration generated from the vibration unit may be transmitted to the surgery unit more easily, and the pressure between an end of the sheath and the ureter may be transmitted to the pressure sensor more easily.

Thus, an energy loss in the transmitting of the vibration may be decreased, and a noise generated when the vibration is transmitted between the axes without coincided with each other, may be decreased. In addition, the transmitting efficiency may be increased. Further, the pressure between the end of the sheath and the ureter is transmitted to the pressure sensor more accurately.

BRIEF DESCRIPTION OF THE DRAWINGS

FIG. 3 is an image showing a vibration unit of the endoscope surgery device of FIG. 1;

FIG. 4 is a perspective view illustrating a surgery unit of the endoscope surgery device of FIG. 1;

REFERENCE NUMERALS

Figure 1:
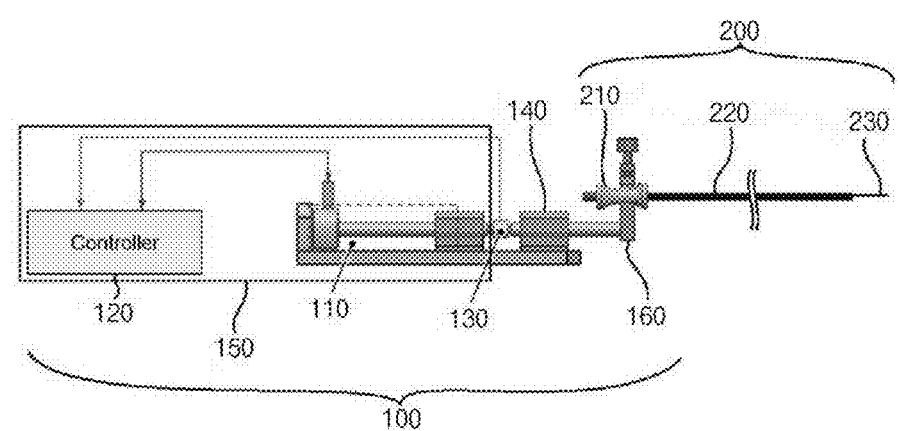
FIG. 1 is a side view illustrating an endoscope surgery device according to the present example embodiment of the present invention.

| | |
|---|---|
| 100, 300: vibration unit | 110, 310: vibration member |
| 120, 320: control member | 130, 330: signal transmitting part |
| 140, 340: pressure sensor | 150, 350: case |
| 152, 352: display | 354: contact sensor |
| 160, 360: vibration transmitting member | 200, 400: surgery unit |
| 210, 410: fixing member | 220, 420: sheath |
| 230, 430: surgery member | |

DETAILED DESCRIPTION

The invention is described more fully hereinafter with Reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention is described more fully hereinafter with reference to the accompanying drawings, in which embodiments of the invention are shown.

Figure 2:
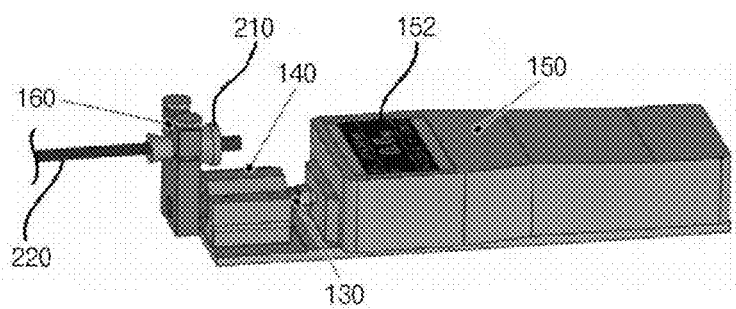
FIG. 2 is a perspective view illustrating the endoscope surgery device of FIG. 1.

FIG. 1 is a side view illustrating an endoscope surgery device according to the present example embodiment of the present invention. FIG. 2 is a perspective view illustrating the endoscope surgery device of FIG. 1.

Referring to FIG. 1 and FIG. 2, the endoscope surgery device according to the present example embodiment includes a vibration unit 100 and a surgery unit 200. The vibration unit 100 is combined with an end of the surgery unit 200, and applies the vibration to the surgery unit 200.

FIG. 3 is an image showing a vibration unit of the endoscope surgery device of FIG. 1.

Referring to FIG. 1, FIG. 2 and FIG. 3, the vibration unit 100 includes a vibration member 110, a control member 120, a signal transmitting part 130, a pressure sensor 140, a case 150 and a vibration transmitting member 160.

The vibration member 110 is electrically connected to the control member 120, and generates a physical vibration based on a vibration signal from the control member 120.

In the present example embodiment, the vibration member 110 generates an ultrasonic vibration along a longitudinal direction of the surgery unit 200. Alternatively, the vibration member 110 may generate the ultrasonic vibration along an inclined direction or a cross-sectional direction of the surgery unit 200.

The vibration member 110 may include an ultrasonic motor (USM), an electric actuator, an electro-magnetic actuator, a piezo actuator, an electrostatic actuator, an elastomer actuator and so on. In the present example embodiment, the vibration member 110 may have vibration intensity between about 100 mV and about 1,000 mV, and have the frequency of vibrations between about 100 Hz and about 20,000 Hz. More specifically, the vibration member 110 may have vibration intensity between about 250 mV and about 500 mV, and have the frequency of vibrations between about 300 Hz and about 18,000 Hz.

The control member 120 is electrically connected to the vibration member 110 and the pressure sensor 140, and controls the supply of the vibration signal to the vibration member 110 based on the pressure signal from the pressure sensor 140. The control member 120 may control the vibration intension generated from the vibration member 110, or may control the generation of the vibration member 110, and may process and save the pressure signal measured by the pressure sensor 140 in the inserting of the sheath 220.

In the present example embodiment, the control member 120 is connected to the pressure sensor 140 through the signal transmitting part 130. The signal transmitting part 130 is physically connected between the vibration member 110 and the pressure sensor 140, to transmit the vibration from the vibration member 110 to the pressure sensor 140. In addition, the signal transmitting part 130 is electrically connected between the control member 120 and the pressure sensor 140, to transmit the pressure signal from the pressure sensor 140 to the control member 120.

Here, when the pressure signal from the pressure senor 140 reaches or over a threshold, the control member 120 stops the vibration signal applied to the vibration member 110 and generates an alarm, to decrease the pressure of the surgery unit 200 by the operator.

When the operator pushes the surgery unit 200 over the predetermined pressure (threshold pressure), an end of the sheath 220 of the surgery unit 200 may pressurize the ureter excessively. Thus, the ureteral mucosa can be injured, or in serious cases, a total ureteral avulsion may occur. In addition, in the long-term, the injured ureteral may lead to devastating surgical complications, such as hydronephrosis or secondary stricture.

Thus, in the present example embodiment, when the end of the sheath 200 of the surgery unit 200 pressurizes the inside wall thereof over the threshold, the vibration is stopped and the sheath 200 is automatically detached from the vibration transmitting member 160. Thus, the pressure applied to the inside wall thereof is decreased and the damage of the inner ureteral mucosa. In addition, the alarm may be generated.

For example, when the end of the sheath 220 of the surgery unit 200 applies the pressure to the ureter over 500 mN, the control member 120 may stop applying the vibration signal and apply a releasing signal to the vibration transmitting member 160, to release the combination between the vibration transmitting member 160 and the fixing member 210. When the combination between the vibration transmitting member 160 and the fixing member 210 is released, the vibration or the pressure is not applied to the sheath 220. The vibration transmitting member 160 may include a motor, an electro-magnetic valve, an actuator and so on for releasing the combination between the vibration transmitting member 160 and the fixing member 210 based on the releasing signal.

The case 150 covers the vibration member 110, the control member 120 and the signal transmitting part 130, and has a longitudinally extending shape for the operator to grip more easily.

A display 150 displaying a vibrating speed, a pressure, an operating time, an surgical procedures state and so on, and an alarm part (not shown) generating the alarm may be configured at outside of the case 150. The display 152 is electrically connected to the control member 120 and displays the signal from the control member 120. The alarm part alarms when the pressure applied to the ureter is over the threshold.

The vibration transmitting member 160 is connected to the pressure sensor 140, and thus, transmits the vibration from the vibration member 110 to the surgery unit 200 and transmits the pressure between the sheath 220 and the ureter to the pressure sensor 140. In the present example embodiment, the vibration transmitting member 160 releases the combination between the vibration transmitting member 160 and the fixing member 210 based on the releasing signal from the control member 120.

An axis of the pressure sensor 140 is not coincided with that of the surgery unit 200. Alternatively, the vibration transmitting member may have a hollow shape, and thus the surgery unit may be combined with an inside of the vibration transmitting member sharing the same axis.

FIG. 4 is a perspective view illustrating a surgery unit of the endoscope surgery device of FIG. 1.

Referring to FIG. 1, FIG. 2, FIG. 3 and FIG. 4, the surgery unit 200 includes a fixing member 210, a sheath 220, a surgery member 230 and a button 235.

The fixing member 210 is combined with the vibration transmitting member 160 of the vibration unit 100, and transmits the vibration from the vibration transmitting member 160 to the sheath 220. Here, the fixing member 210 may be detachably combined with the vibration transmitting member 160 with various kinds of combinations like a screw, a zig and so on.

The surgery unit 200 is inserted into the ureter for the surgery, and thus the surgery unit 200 is detached from the vibration unit 100 for falling into disuse or being sterilized for the reuse after the surgery. Thus, in the present example embodiment, the fixing member 210 is to be detached from the vibration transmitting member 160, and thus the surgery unit 200 may be easily detached and be replaced.

The sheath 220 is combined with the fixing member 210, and has a tube shape extending along a longitudinal direction. The sheath 220 is inserted into the ureter and is penetrated into a surgery portion, and thus may have various kinds of diameter or lengths.

The sheath 220 has a hollow shape so that the surgery member 230 may pass through the sheath 220. Since an outer diameter of the sheath 220 is larger than a width of the surgery member 230, the outer diameter of the sheath 220 may be larger than the diameter of the ureter.

In the present example embodiment, the vibration from the vibration unit 100 is transmitted to the sheath 220, and thus a friction force between the outer surface of the sheath 220 and the ureter may be decreased.

The reason why the friction force is decreased is explained as follows.

First, the friction force is decreased when an object is vibrated. Generally, a kinetic friction coefficient is smaller than a static friction coefficient, and thus the applied pressure is also decreased when the kinetic friction coefficient is applied between the sheath 220 and the ureter.

Second, the pressure applied to the sheath 220 is dissipated or decreased due to the vibration of the sheath 220. Even though the pressure is applied between the sheath 220 and the ureter, the ureter is physically pushed when the sheath 220 is vibrated. Thus, the pushed ureter may be rearranged, so that the applied pressure may be dissipated or decreased.

In the present example embodiment, the vibration from the vibration unit 100 is entirely applied to the sheath 220, and thus an end portion at which the sheath 200 is inserted and a middle portion at which the sheath 200 passes through are prevented from being damaged. For example, a stress may be concentrated at a portion where ureter meets ureterovesical junction or at a portion where bladder meets urethra, and thus the concentrated stress may be easily decreased due to the vibration of the sheath 220.

The surgery member 230 is disposed inside of the sheath 220, and an end of the surgery member 230 is protruded from the end of the sheath 220. A surgery device such as an endoscope camera, a laser, an ultrasonic impact part, a needle and so on, may be disposed at the end of the surgery member 230.

The button 235 is connected to an opposite end of the surgery member 230, to control the surgical procedures of the surgery member 230. In the present example, the button 235 is protruded to an outside of the fixing member 210, and thus the button 235 may be easily controlled when the sheath 220 is inserted.

Figure 5:
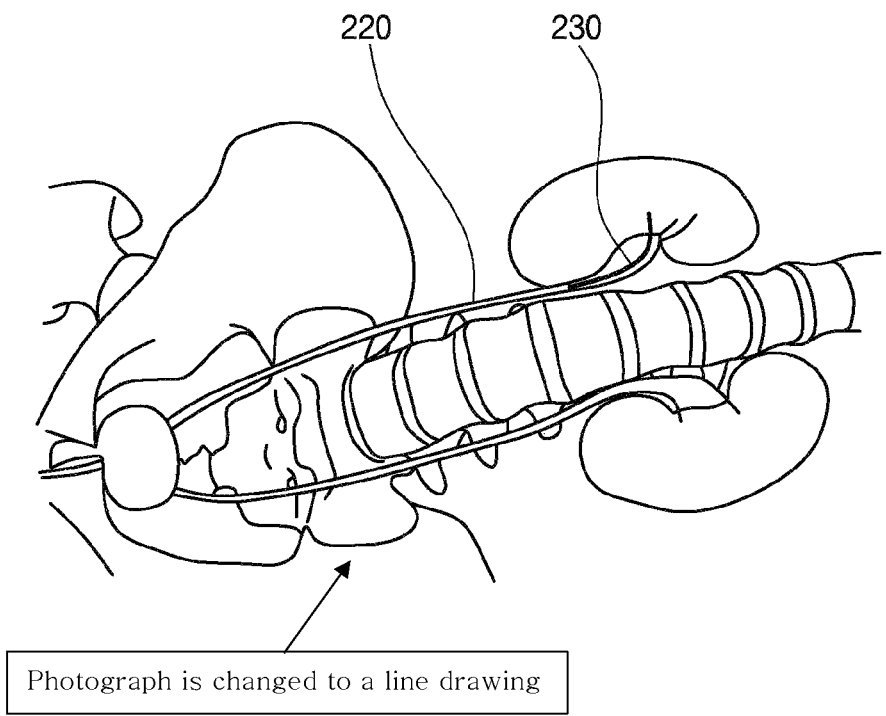
FIG. 5 is an image showing a surgery using the surgery unit of FIG. 4.

FIG. 5 is an image showing a surgery using the surgery unit of FIG. 4.

Referring to FIG. 1, FIG. 2, FIG. 3, FIG. 4 and FIG. 5, the control member 120 applies the vibration signal to the vibration member 110, when a switch (not shown) of the vibration unit 100 is ON.

The vibration generated by the vibration member 110 is applied to the vibration transmitting member 160 through the signal transmitting part 130 and the pressure sensor 140.

The vibration applied to the vibration transmitting member 160 is transmitted to the fixing member 210 combined with the vibration transmitting member 160.

The vibration transmitted to the fixing member 210 is entirely applied to the sheath 220 connected to the fixing member 210.

The vibration entirely applied to the sheath 220 decreases the friction force between the outer surface of the sheath 220 and the ureter, when the sheath 220 is inserted into the (ureter.

The pressure between the end of the sheath 220 and the ureter is applied to the pressure sensor 140 through the sheath 220, the fixing member 210 and the vibration transmitting member 160.

The pressure sensor 140 generates the pressure signal corresponding to the applied pressure, and applies the pressure signal to the control member 120 through the signal transmitting member 130.

The control member 120 analyzes the applied pressure signal, and then stops transmitting the vibration signal and generates the alarm when the pressure between the end of the sheath 220 and the ureter.

Figure 6:
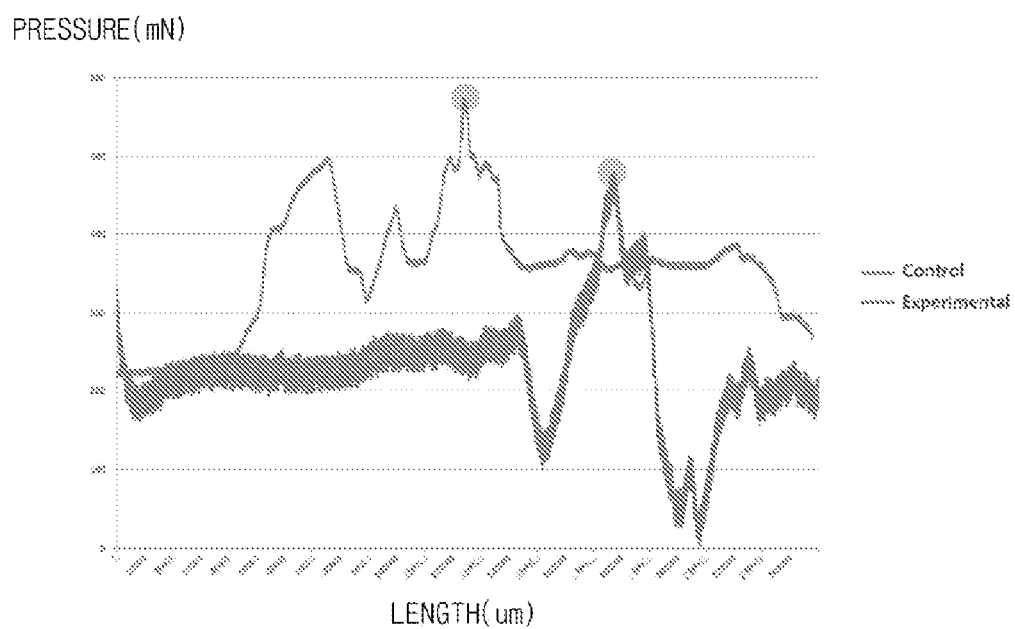
FIG. 6 is a graph showing a state of the surgery using the endoscope surgery device in FIG. 1.

FIG. 6 is a graph showing a state of the surgery using the endoscope surgery device in FIG. 1. Here, the experiment was performed using the urethra, bladder, and the bladder of a pig which has organs similar to human beings.

Referring to FIG. 6, the pressure applied to the pressure sensor 140 is measured, when the vibration is not applied to the sheath 220 and when the vibration is applied to the sheath 220.

When the vibration is not applied to the sheath 220, the maximum pressure applied to the pressure sensor 140 is about 570 mN, and an average pressure is about 370 mN.

When the vibration is applied to the sheath 220, the maximum pressure applied to the pressure sensor 140 is about 480 mN, and an average pressure is about 230 mN.

Accordingly, with the vibration, the maximum pressure is decreased by about 15%, and the average pressure is decreased by about 36%.

Table 1 shows the average inserting pressure according to vibration intensity and the frequency of vibration.

As shown in Table 1, when the ultrasonic vibration with the vibration intensity of 250 mV and the frequency of vibration of 18,000 Hz is applied, the average inserting pressure is decreased by about 36.4%.

Table 2 shows the experimental results of the average inserting pressure on twelve Yorkshire porcine models having a weight between about 35 kg and about 40 kg, when the vibration intensity of 250 mV and the frequency of vibration of 18,000 Hz are applied.

TABLE 2

| PIG Nm | No vibration (mN) | vibration with 250 mV and 18,000 Hz (mN) | reduction rate (%) |
|---|---|---|---|
| 1 | 251 | 161 | 35.86 |
| 2 | 218 | 146 | 33.03 |
| 3 | 658 | 291 | 55.78 |
| 4 | 271 | 168 | 38.01 |
| 5 | 648 | 491 | 24.23 |
| 6 | 559 | 445 | 20.39 |
| 7 | 244 | 144 | 40.98 |
| 8 | 114 | 65.7 | 42.37 |
| 9 | 121 | 96.3 | 20.41 |
| 10 | 753 | 601 | 20.19 |
| 11 | 174 | 84.3 | 51.55 |
| 12 | 201 | 111 | 44.78 |

As shown in Table 2, the experimental results show that average inserting pressure is decreased by about 36.9% when the vibration with the above mentioned condition is applied.

Accordingly, the endoscope surgery device according to the present example embodiment may decrease the risk of ureteral injury during surgery.

In addition, the vibration is applied to the sheath 220 of the endoscope surgery device, and thus the friction force between the ureter and the sheath 220 may be decreased. Thus, the sheath 220 may be inserted into the ureter more easily and the damage to the ureteral mucosa may be prevented.

In addition, the pressure sensor 140 is configured to stop vibrating when the applied vibration on the sheath 220 is

TABLE 1

| PIG Nm | Position of urethral canal | vibration intensity | No vibration | 300 Hz | 500 Hz | 1,000 Hz | 8,000 Hz | 18,000 Hz |
|---|---|---|---|---|---|---|---|---|
| 1 | Right | 250 mV | 223 | 169 mN | 153 mN | 160 mN | 145 mN | 145 mN |
|   |       | 500 mV |     | 192 mN | 179 mN | 177 mN | 154 mN | 154 mN |
|   | Left  | 250 mV | 252 | 192 mN | 167 mN | 156 mN | 158 mN | 161 mN |
|   |       | 500 mV |     | 229 mN | 216 mN | 165 mN | 168 mN | 161 mN |
| 2 | Right | 250 mV | 274 | 178 mN | 172 mN | 178 mN | 170 mN | 170 mN |
|   |       | 500 mV |     | 214 mN | 203 mN | 196 mN | 203 mN | 195 mN |
|   | Left  | 250 mV | 518 | 334 mN | 247 mN | 200 mN | 216 mN | 215 mN |
|   |       | 500 mV |     | 386 mN | 380 mN | 288 mN | 224 mN | 272 mN |
| 3 | Right | 250 mV | 703 | 560 mN | 488 mN | 439 mN | 457 mN | 445 mN |
|   |       | 500 mV |     | 578 mN | 409 mN | 399 mN | 383 mN | 342 mN |
|   | Left  | 250 mV | 663 | 610 mN | 488 mN | 480 mN | 455 mN | 491 mN |
|   |       | 500 mV |     | 562 mN | 485 mN | 430 mN | 401 mN | 429 mN |

In the experiment of Table 1, the vibration intensity of the vibration member is 250 mV or 500 mV, and the ultrasonic vibration having the frequency of vibration between 300 Hz and 18,000 Hz is applied to the sheath 220. In addition, left and right ureters of three similar pigs were used.

increased over the threshold, and the combination between the vibration unit and the surgery unit is automatically released. Thus, an additional insertion may be prevented and the damage to the ureteral mucosa may be prevented or minimized.

Figure 7:
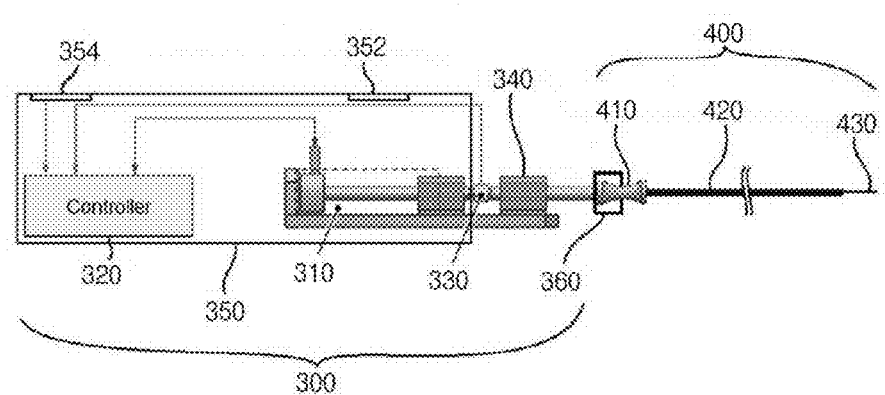
FIG. 7 is a side view illustrating an endoscope surgery device according to another example embodiment of the present invention.

FIG. 7 is a side view illustrating an endoscope surgery device according to another example embodiment of the present invention.

The endoscope surgery device according to the present example embodiment is substantially same as the endoscope surgery device according to the previous example embodiment in FIGS. 1 to 6, except for a control member 320, a vibration transmitting member 360 and a contact sensor 354, and thus same reference numerals are used for same elements and repetitive explanation will be omitted.

Referring to FIG. 7, the endoscope surgery device according to the present example embodiment includes a vibration unit 300 and a surgery unit 400. The vibration unit 300 is combined with an end of the surgery unit 400, and applies the vibration to the surgery unit 400.

The vibration unit 300 includes a vibration member 310, a control member 320, a signal transmitting part 330, a pressure sensor 340, a contact sensor 354 and a case 350.

The control member 320 is electrically connected to the vibration member 310, the pressure sensor 340 and the contact sensor 354, and controls the supply of the vibration signal to the vibration member 310 based on the pressure signal from the pressure sensor 340 and the contact signal from the contact sensor 354.

Here, when the pressure signal from the pressure sensor 340 reaches or over a threshold, the control member 320 stops the vibration signal applied to the vibration member 310 and generates an alarm, to decrease the pressure of the surgery unit 400 by the operator.

The contact sensor 354 is disposed on outer surface of the case 350, to sense the contact of a hand of the operator. For example, the contact sensor 354 may be a touch sensor, capacitor sensor, a piezo sensor and so on.

In the present example embodiment, when the contact signal applied from the contact sensor is rapidly changed, the control member 320 stops the vibration signal applied to the vibration member 310. In the present example embodiment, the vibration is generated by the vibration member 310, and thus the friction force between the hand of the operator and the case 350 may be rapidly decreased.

When the friction force between the hand of the operator and the case 350 is rapidly decreased, the hand of the operator is slipped from the case 350. Thus, in the present example embodiment, the vibration is stopped to prevent the damage of the ureter due to the slip of the hand from the case 350.

The case 350 covers the vibration member 310, the control member 320 and the signal transmitting part 330, and has a longitudinally extending shape for the operator to grip more easily.

A display 352 displaying a vibrating speed, a pressure, an operating time, an surgical procedures state and so on, and an alarm part (not shown) generating the alarm may be configured at outside of the case 350.

The vibration transmitting member 360 is connected to the pressure sensor 340, and thus, transmits the vibration from the vibration member 310 to the surgery unit 200 and transmits the pressure between the sheath 420 and the ureter to the pressure sensor 340.

The vibration transmitting member 360 includes a receiving space at a center, and receives and combines the fixing member 410 of the surgery unit 400.

The vibration transmitting member 360 connects the pressure sensor 340 with the surgery unit 400, and an axis of the pressure sensor 340 is coincided with that of the surgery unit 400. In the present example embodiment, the vibration member 310, the signal transmitting part 330, the pressure sensor 340, the vibration transmitting member 360 and the surgery unit 400 share the same axis, and thus the vibration generated from the vibration member 310 sequentially passes through the signal transmitting part 330, the pressure sensor 340 and the vibration transmitting member 360 and then is applied to the surgery unit 400, more easily and more correctly. In addition, the pressure between the end of the sheath 420 and the ureter passes through the vibration transmitting member 360 to be applied to the pressure sensor 340 more easily and more correctly.

The surgery unit 400 includes a fixing member 410, a sheath 420, a surgery member 430 and a button (not shown).

The fixing member 410 is combined with the vibration transmitting member 460 of the vibration unit 400, and transmits the vibration from the vibration transmitting member 460 to the sheath 420. Here, the fixing member 410 may be detachably combined with the vibration transmitting member 460 with various kinds of combinations like a screw, a zig and so on.

The sheath 420 is combined with the fixing member 410, and has a tube shape extending along a longitudinal direction. The sheath 420 is inserted into the ureter and is penetrated into a surgery portion, and thus may have various kinds of diameter or lengths.

The sheath 420 has a hollow shape so that the surgery member 430 may pass through the sheath 220.

In the present example embodiment, the vibration from the vibration unit 300 is transmitted to the sheath 420, and thus a friction force between the outer surface of the sheath 420 and the ureter may be decreased.

Accordingly, the vibration member 310, the signal transmitting part 330, the pressure sensor 340, the vibration transmitting member 360 and the surgery unit 400 share the same axis, and thus the vibration generated from the vibration member 310 sequentially passes through the signal transmitting part 330, the pressure sensor 340 and the vibration transmitting member 360 and then is applied to the surgery unit 400, more easily and more correctly. In addition, the pressure between the end of the sheath 420 and the ureter passes through the vibration transmitting member 360 to be applied to the pressure sensor 340 more easily and more correctly.

Thus, an energy loss in the transmitting of the vibration may be decreased, and a noise generated when the vibration is transmitted between the axes without coincided with each other, may be decreased. In addition, the transmitting efficiency may be increased. Further, the pressure between the end of the sheath and the ureter is transmitted to the pressure sensor more accurately.

According to the present example embodiments, a vibration is applied to a sheath of an endoscope surgery device, and thus a friction force between the ureter and the sheath may be decreased. Thus, the sheath may be inserted into the ureter more easily and the damage to the ureter may be prevented or minimized.

In addition, a pressure sensor is configured to stop vibration when the applied vibration on the sheath is increased over a threshold, and the combination between a vibration unit and a surgery unit is automatically released. Thus, further excessive placement of the sheath may be prevented and the damage of the ureter may be prevented.

In addition, a fixing member and a vibration transmitting member are detachably combined with each other, and thus the fixing member and the vibration transmitting member may be easily replaced.

In addition, the vibration unit and the surgery unit share the same axis, and thus the vibration generated from the vibration unit may be transmitted to the surgery unit more easily, and the pressure between an end of the sheath and the ureter may be transmitted to the pressure sensor more easily.

Thus, an energy loss in the transmitting of the vibration may be decreased, and a noise generated when the vibration is transmitted between the axes without coincided with each other, may be decreased. In addition, the transmitting efficiency may be increased. Further, the pressure between the end of the sheath and the ureter is transmitted to the pressure sensor more accurately.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. An endoscope surgery device comprising:
a vibration unit generating a vibration;
a surgery unit comprising a sheath and a surgery member,
wherein the sheath has a tube shape with a hollow extended in a longitudinal direction, and is entirely vibrated due to the vibration from the vibration unit when inserted into the ureter,
wherein the surgery unit passes through the hollow of the sheath, and is extended to an end of the sheath for an surgical procedures on the ureter,
wherein the vibration unit comprises:
a vibration member generating the vibration;
a pressure sensor disposed between the vibration member and the surgery unit, to measure an inserting pressure of the surgery unit; and
a control member configured to control the vibration of the vibration member, when the measured pressure from the pressure sensor is over a threshold.

2. The endoscope surgery device of claim 1, wherein the vibration unit generates an ultrasonic vibration.

3. The endoscope surgery device of claim 1, wherein the vibration unit vibrates the sheath along the longitudinal direction.

4. The endoscope surgery device of claim 1, wherein the vibration unit comprises:
a vibration transmitting member disposed between the pressure sensor and the surgery unit, and fixed to an end of the surgery unit.

5. The endoscope surgery device of claim 4, wherein an axis of the pressure sensor is not coincided with that of the surgery unit.

6. The endoscope surgery device of claim 4, wherein the vibration member and the pressure sensor have the same axis coincided with the axis of the sheath.

7. The endoscope surgery device of claim 1, wherein the vibration unit further comprises a contact sensor sensing a contacting state of a hand of an operator,
wherein the control member is configured to stop the vibration of the vibration unit when the hand of the operator is slipped from a surface of the vibration unit.

* * * * *